(12) United States Patent
Motoki (10) Patent No.: US 7,554,082 B2
(45) Date of Patent: Jun. 30, 2009

(54) PATTERN OBSERVATION APPARATUS, PATTERN OBSERVATION METHOD, METHOD OF MANUFACTURING SEMICONDUCTOR DEVICE, AND PROGRAM

(75) Inventor: Hiroshi Motoki, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 273 days.

(21) Appl. No.: 11/528,589

(22) Filed: Sep. 28, 2006

(65) Prior Publication Data

US 2007/0085006 A1    Apr. 19, 2007

(30) Foreign Application Priority Data

Sep. 30, 2005   (JP) ............................. 2005-287487

(51) Int. Cl.
  *G01N 23/00* (2006.01)
  *G21K 7/00* (2006.01)
  *A61N 5/00* (2006.01)
  *G21G 5/00* (2006.01)

(52) U.S. Cl. .................... 250/307; 250/310; 250/492.2; 250/492.3; 250/311; 250/306

(58) Field of Classification Search ................ 250/306, 250/307, 310, 311, 492.2, 442.11, 559.4, 250/492.3; 345/660, 663, 678; 382/145, 382/148, 149

See application file for complete search history.

(56) References Cited

U.S. PATENT DOCUMENTS

| | | | |
|---|---|---|---|
| 6,724,005 B2 | | 4/2004 | Tokumoto |
| 6,897,444 B1 * | 5/2005 | Adler | ........................ 250/310 |
| 7,212,017 B2 * | 5/2007 | Watanabe et al. | ........... 324/751 |
| 7,253,645 B2 * | 8/2007 | Talbot et al. | ................. 250/310 |
| 2004/0069956 A1 * | 4/2004 | Takane et al. | ............. 250/492.1 |
| 2004/0094713 A1 * | 5/2004 | Nakada et al. | .............. 250/310 |
| 2004/0158409 A1 | 8/2004 | Teshima et al. | |
| 2005/0104017 A1 * | 5/2005 | Kimba et al. | .......... 250/559.07 |
| 2005/0242286 A1 * | 11/2005 | Watanabe et al. | ........... 250/310 |

* cited by examiner

*Primary Examiner*—Jack I Berman
*Assistant Examiner*—Brooke Purinton
(74) *Attorney, Agent, or Firm*—Finnegan, Henderson, Farabow, Garrett & Dunner, L.L.P.

(57) ABSTRACT

A pattern observation apparatus includes: a defect position information input unit which downloads defect position information for a pattern, the defect position information having been detected by an external inspection apparatus with regard to a specimen in which the pattern is formed; a moving unit which moves the specimen so as to bring a place detected as defective by the inspection apparatus into a field of view on the basis of the defect position information; a charged particle source which generates a charged particle beam and applies the charged particle beam to the specimen; a signal processing unit which detects at least one of secondary charged particles, reflected charged particles and back scattering charged particles emitted from the specimen due to the application of the charged particle beam and which outputs data on an inspection image of a specimen surface in the defective place; an inspection unit which re-detects an abnormality of the place detected as defective, on the basis of the inspection image; and a view field adjusting unit which adjusts an image size or the number of pixels in accordance with accuracy distribution of the defect position information in the inspection apparatus while a resolution is kept fixed.

20 Claims, 5 Drawing Sheets

512×512 PIXELS

FIG. 6A

1024×1024 PIXELS

FIG. 6B

1024×512 PIXELS

PATTERN OBSERVATION APPARATUS, PATTERN OBSERVATION METHOD, METHOD OF MANUFACTURING SEMICONDUCTOR DEVICE, AND PROGRAM

CROSS REFERENCE TO RELATED APPLICATION

This application claims benefit of priority under 35USC §119 to Japanese patent application No. 2005-287487, filed on Sep. 30, 2005, the contents of which are incorporated by reference herein.

BACKGROUND OF THE INVENTION

1. Field of the Invention

The present invention relates to a pattern observation apparatus, a pattern observation method, a method of manufacturing a semiconductor device, and a program.

2. Related Background Art

When information on a defect detected by a pattern inspection apparatus is loaded into a scanning electron microscope (hereinafter simply referred to as an "SEM") to observe the defect in more detail, the defect may not come into a field of view if the coordinate accuracy of the inspection apparatus is poor. In this case, it is necessary to enlarge the field of view, but simply decreasing the magnification increases a pixel size and reduces defect detection sensitivity. Thus, the number of pixels has heretofore been increased while the magnification is kept fixed in order to enlarge the field of view.

However, if the number of pixels per direction is simply multiplied by n, an image acquiring time is multiplied by n×n, so that there has been a disadvantage that a throughput is significantly decreased.

As another method, there is a technique in which when a defect can not be detected within a field of view, regions on the periphery of the field of view are searched. However, this method requires as much extra observation time in proportion to the number of times that the searches are conducted, and there has still been a problem of a decreased throughput.

Furthermore, there is a technique for correcting coordinates on the basis of individual data on the basis of the coordinate accuracy of the pattern inspection apparatus. However, the corrected data needs to be modified in accordance with changes with time in the coordinate accuracy of the pattern inspection apparatus and every time maintenance is done on the apparatus, so that there has been a problem that troublesome operations are demanded.

SUMMARY OF THE INVENTION

According to a first aspect of the present invention, there is provided a pattern observation apparatus comprising:

a defect position information input unit which downloads defect position information for a pattern, the defect position information having been detected by an external inspection apparatus with regard to a specimen in which the pattern is formed;

a moving unit which moves the specimen so as to bring a place detected as defective by the inspection apparatus into a field of view on the basis of the defect position information;

a charged particle source which generates a charged particle beam and applies the charged particle beam to the specimen;

a signal processing unit which detects at least one of secondary charged particles, reflected charged particles and back scattering charged particles emitted from the specimen due to the application of the charged particle beam and which outputs data on an inspection image of a specimen surface in the defective place;

an inspection unit which re-detects an abnormality of the place detected as defective, on the basis of the inspection image; and a view field adjusting unit which adjusts an image size or the number of pixels in accordance with accuracy distribution of the defect position information in the inspection apparatus while a resolution is kept fixed.

According to a second aspect of the present invention, there is provided a pattern observation method comprising:

moving a specimen on the basis of defect position information for a pattern formed in the specimen, the defect position information having been obtained by an inspection apparatus with regard to the specimen and generating a charged particle beam at a position where a place detected as defective by the inspection apparatus comes into a field of view to apply the charged particle beam to the specimen;

detecting at least one of secondary charged particles, reflected charged particles and back scattering charged particles emitted from the specimen due to the application of the charged particle beam to acquire an inspection image of a specimen surface in the place detected as defective;

re-detecting an abnormality of the place detected as defective on the basis of the inspection image; and adjusting an image size or the number of pixels in accordance with accuracy distribution of the defect position information dependent on the inspection apparatus while a resolution is kept fixed.

According to a third aspect of the present invention, there is provided a program which is stored in a computer-readable medium connectable to a charged particle microscope and which causes the computer to execute a pattern observation method, said pattern observation method comprising:

moving a specimen on the basis of defect position information for a pattern formed in the specimen, the defect position information having been obtained by an inspection apparatus with regard to the specimen and generating a charged particle beam at a position where a place detected as defective by the inspection apparatus comes into a field of view to apply the charged particle beam to the specimen;

detecting at least one of secondary charged particles, reflected charged particles and back scattering charged particles emitted from the specimen due to the application of the charged particle beam to acquire an inspection image of a specimen surface in the place detected as defective;

re-detecting an abnormality of the place detected as defective on the basis of the inspection image; and adjusting an image size or the number of pixels in accordance with accuracy distribution of the defect position information dependent on the inspection apparatus while a resolution is kept fixed.

According to a fourth aspect of the present invention, there is provided a method of manufacturing a semiconductor device comprising a pattern observation method, said pattern observation method including:

moving a specimen on the basis of defect position information for a pattern formed in the specimen, the defect position information having been obtained by an inspection apparatus with regard to the specimen and generating a charged particle beam at a position where a place detected as defective by the inspection apparatus comes into a field of view to apply the charged particle beam to the specimen;

detecting at least one of secondary charged particles, reflected charged particles and back scattering charged particles emitted from the specimen due to the application of the charged particle beam to acquire an inspection image of a specimen surface in the place detected as defective;

re-detecting an abnormality of the place detected as defective on the basis of the inspection image; and adjusting an image size or the number of pixels in accordance with accuracy distribution of the defect position information dependent on the inspection apparatus while a resolution is kept fixed.

DETAILED DESCRIPTION OF THE INVENTION (1) How the Present Invention is Devised

Before describing embodiments of the present invention, details on how the inventor of the present application has devised the present invention will be described with reference to FIG. 1 to FIG. 3.

Figure 1:
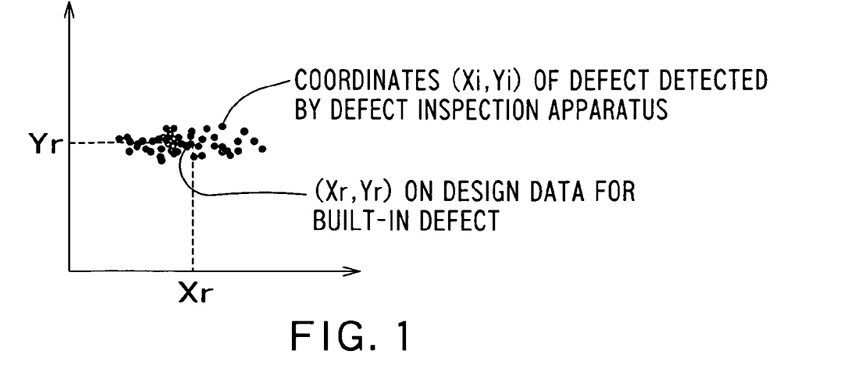
FIG. 1 is a diagram showing one example of accuracy distribution of defect positions detected by a defect inspection apparatus.

FIG. 1 is a diagram showing one example of accuracy distribution of defect positions detected by a defect inspection apparatus. In the present example, a specimen targeted for inspection has been created in the following manner: a defect is previously built into design data for a semiconductor pattern, and the pattern containing the defect is transferred onto a wafer. Such a specimen is inspected by the defect inspection apparatus, and coordinates of the detected defect and coordinates on the design data are plotted on the same graph for easier comparison. In FIG. 1, a coordinate position of the built-in defect on the design data is shown for each die (Xr, Yr), and if the number of dies is n, coordinates of the defect detected by the defect inspection apparatus are (Xi, Yi (1≦i≦n)). It is possible to read from FIG. 1 that the positional accuracy of the defect is poor only in one direction (X direction). This corresponds to a beam scan direction and a stage scan direction of the defect inspection apparatus. Moreover, there is an inspection apparatus in which the surface shape of a beam applied to the wafer is elliptic or linear in order to reduce inspection time, and in this case, it has been revealed that defect position accuracy in the direction of the major axis of the beam is poor. Thus, the amount of positional difference of the defect may have a tendency to depend on a poor quality of the accuracy in a particular direction rather than on normal distribution.

Figure 2A:
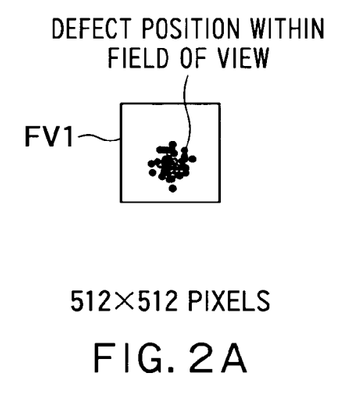
FIGS. 2A and 2B are diagrams for explaining the relations between a view field size and the number of pixels under the same resolution.
Figure 2B:
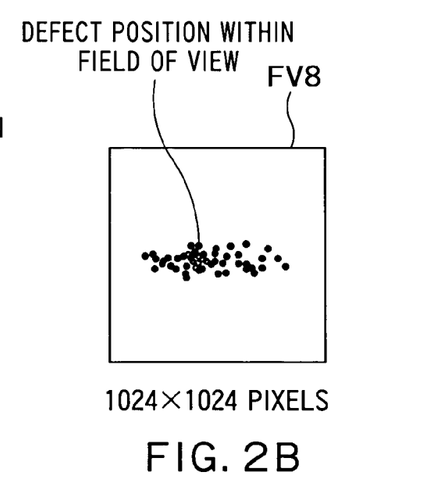
Figure 3:
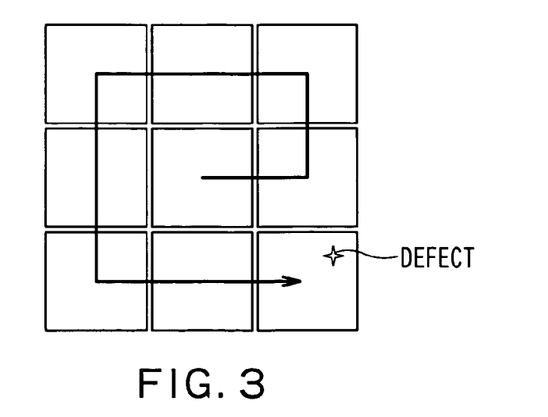
FIG. 3 is a diagram showing one example of defect searching method according to a prior art.

Next, FIGS. 2A and 2B are diagrams for explaining, in association with the positional accuracy of the defect, the relations between a view field size and the number of pixels when the detected defect is observed in detail by an SEM. If the magnification is changed to adjust a field of view, the resolution of an image, that is, the size (magnification) per image is changed, and defect detection sensitivity is thus affected. In this case, under the present circumstances, the number of pixels is increased or decreased to adjust the field of view, for example, from a field of view FV1 in FIG. 2A to a field of view FV8 in FIG. 2B. However, if the number of pixels per direction is multiplied by n, an image acquiring time is multiplied by n×n, so that there is a disadvantage that a throughput is significantly decreased. It is possible to conceive a method of searching peripheral regions without changing the magnification and the number of pixels only when the defect can not be detected. However, searching the adjacent eight regions one by one is inefficient, and as shown in, for example, FIG. 3, nine image acquisitions are required including the first inspection region in the worst case.

Therefore, the inventor of the present application has focused attention on the fact that the amount of positional difference of the defect does not have normal distribution and has a tendency to depend on a poor quality of the accuracy in a particular direction, so that the inventor of the present application has considered that the enlargement of the field of view only in the direction with poor positional accuracy can reduce the image acquiring time when positional accuracy distribution of the defect is known in advance. Further, the inventor of the present application has found out that the efficiency is improved if the search is carried out so that priority is given to the direction in which the positional accuracy of the defect is poor, in the case where the peripheral regions are searched only when the defect can not be detected without changing both the magnification and the number of pixels while the resolution is kept fixed.

The inventor has devised the present invention on the basis of the above-mentioned findings. Hereinafter, some of the embodiments of the present invention will be described in detail with reference to FIG. 4 to FIG. 8.

It is to be noted that a case is described in the following embodiments where an electron beam is used as a charged particle beam, but the present invention is not limited thereto and can also be applied to a case where, for example, an ion beam is used.

(2) One Embodiment of Pattern Observation Apparatus

Figure 4:
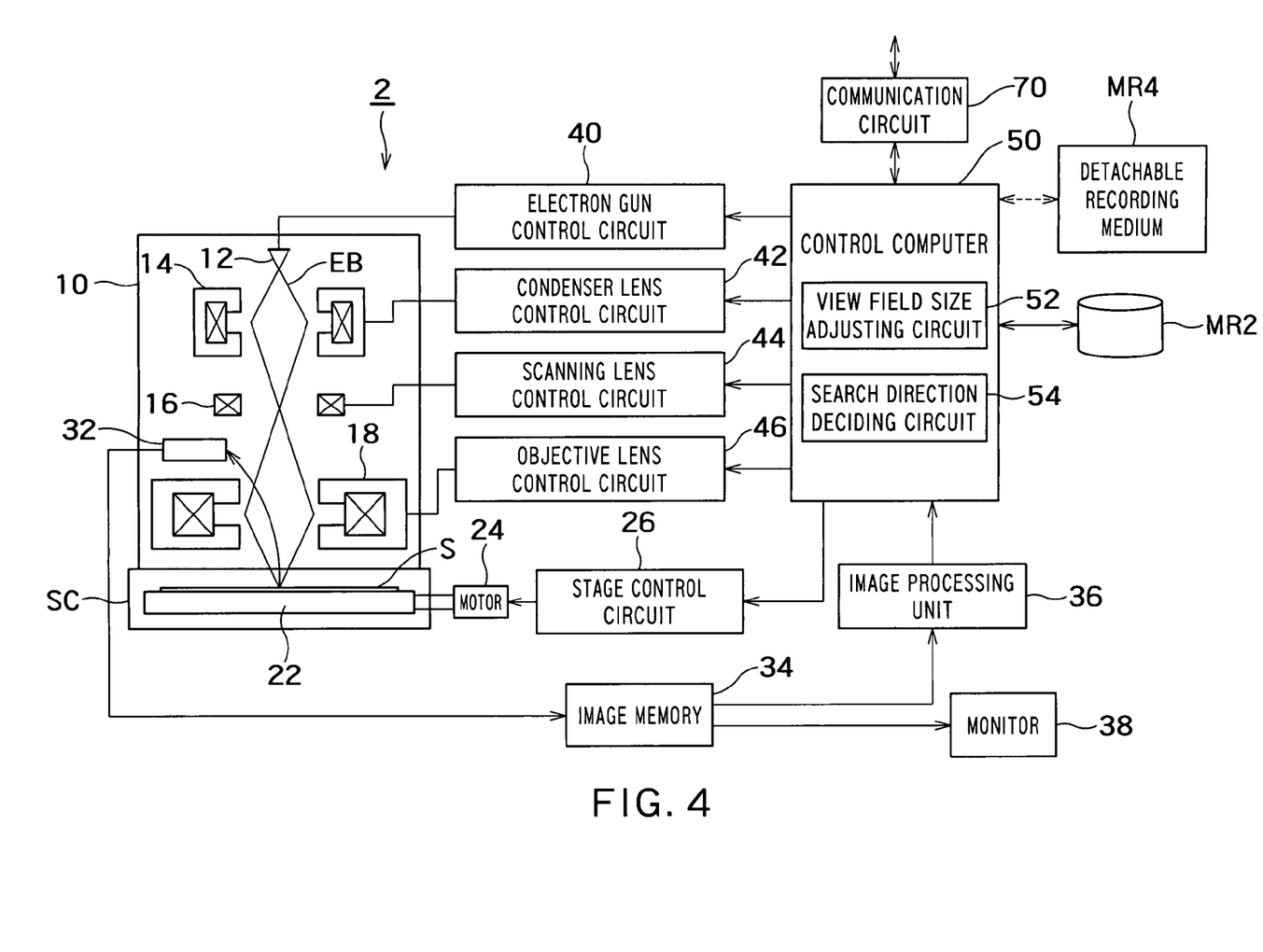
FIG. 4 is a block diagram showing a schematic configuration of a pattern observation apparatus in a first embodiment according to the present invention.

FIG. 4 is a block diagram showing a schematic configuration of a pattern observation apparatus in one embodiment according to the present invention. A pattern observation apparatus 2 shown in FIG. 4 is an application of a scanning electron microscope which scans a specimen with a focused electron beam EB to observe a semiconductor pattern formed on the specimen. Being provided with defect position information from an external inspection apparatus, the pattern observation apparatus 2 operates so that the position of a defect on a specimen comes within the field of view thereof, and acquires an image of the defect, and then specifies the defect position and conducts a reinspection. The pattern observation apparatus 2 comprises an electron beam column 10, various control circuits 40, 42, 44 and 46, an XY stage 22 supporting a semiconductor substrate which is a specimen (hereinafter referred to as "inspection substrate") S, a motor 24, a stage control circuit 26, a detector 32, an image memory 34, an image processing unit 36, a monitor 38, a control computer 50, a communication circuit 70, and a recording medium MR2 previously incorporated in the apparatus. In this embodiment the communication circuit 70 corresponds to, for example, defect position information input unit. Further, in this embodiment the XY stage 22, the motor 24 and the stage control circuit 26 correspond to, for example, moving unit. Moreover, in this embodiment the detector 32 corresponds to, for example, signal processing unit, and the image processing unit 36 corresponds to, for example, inspection unit.

The control computer 50 comprises a view field size adjusting circuit 52 and a search direction deciding circuit 54. In this embodiment the view field size adjusting circuit 52 and the search direction deciding circuit 54 correspond to, for example, view field adjusting unit. Further, the control computer 50 controls the entire apparatus via the various control circuits 40, 42, 44 and 46, the stage control circuit 26, etc.

The recording medium MR2 stores data used for alignment (positioning) of the inspection substrate S. This alignment data is transmitted from the external defect inspection apparatus (not shown) to the control computer 50 via the communication circuit 70, and stored in the recording medium MR2 by the control computer 50. The recording medium MR2 also stores coordinate data for the defect in the inspection substrate S detected by the external defect inspection apparatus (not shown). This defect coordinate data is also transmitted to the control computer 50 via the communication circuit 70, and stored in the recording medium MR2 by the control computer 50. Further, accuracy distribution data in the defect coordinate data peculiar to the external defect inspection apparatus (not shown) is also stored in the recording media MR2 and MR4 via the communication circuit 70 and the control computer 50. The alignment data, the defect coordinate data and the accuracy distribution data will be described later in detail. It is to be noted that instead of storing these data in the previously attached recording medium MR2 via the communication circuit 70 and the control computer 50, the data may be input off line in the detachable recording medium MR4 shown together in FIG. 4 from the external defect inspection apparatus (not shown), and the detachable recording medium MR4 may be connected to the control computer 50 at every reinspection.

The electron beam column 10 includes an electron gun 12, a condenser lens 14, a scanning lens 16 and an objective lens 18. The electron gun 12 generates the electron beam EB when receiving a control signal from the electron gun control circuit 40, and applies the electron beam EB to the inspection substrate S. The condenser lens 14 excites a magnetic field and an electric field when receiving a control signal from the condenser lens control circuit 42, and focuses the electron beam EB so that a proper beam diameter is achieved. The objective lens 18 excites a magnetic field and an electric field in accordance with a control signal from the objective lens control circuit 46, and again focuses the electron beam EB so that this electron beam is applied in just focus onto the inspection substrate S. The scanning lens 16 excites a magnetic field and an electric field for deflecting the electron beam EB when receiving a control signal from the scanning lens control circuit 44, thereby two-dimensionally scanning the inspection substrate S with the electron beam EB. The motor 24 operates in response to a control signal from the stage control circuit 26, and moves the XY stage 22 within an XY plane.

The detector 32 detects secondary electrons, reflected electrons and back scattering electrons generated from the inspection substrate S due to the application of the electron beam EB. Output signals of the detector 32 constitute a two-dimensional image representing the state of the surface of the inspection substrate S, and data on this two-dimensional image is stored in the image memory 34.

The data on the two-dimensional image is output from the image memory 34 to the monitor 38, and the two-dimensional image is displayed and serves in the observation of the wafer surface and is also output to the image processing unit 36.

The image processing unit 36 compares the alignment data taken by the control computer 50 from the recording medium MR2 with the data on the inspection image supplied from the image memory 34, and the image processing unit 36 calculates an amount of difference between coordinate systems of these data and supplies an obtained value to the control computer 50. Receiving the obtained value from the image processing unit 36, the control computer 50 supplies an instruction signal to at least one of the scanning lens control circuit 44 and the stage control circuit 26 to use at least one of the scanning lens 16 and the XY stage 22 for the correction of the difference amount.

The control computer 50 includes the view field size adjusting circuit 52 and the search direction deciding circuit 54 which are characteristic components in the present embodiment. The view field size adjusting circuit 52 generates a control signal for adjusting an image size and the number of images so that a field of view for reinspection is deformed independently in a vertical direction and in a horizontal direction on the basis of the accuracy distribution data for the defect coordinates taken from the recording medium MR2, and then the view field size adjusting circuit 52 transmits the control signal to the scanning lens control circuit 44. Moreover, when the defect can not be detected within the first field of view in the reinspection, the search direction deciding circuit 54, instead of changing the size of the field of view, decides in which direction to search by priority, and thus generates a control signal and transmits the control signal to the scanning lens control circuit 44.

The operation of the pattern observation apparatus 2 shown in FIG. 4 will be described as an embodiment of a pattern observation method according to the present invention with reference to FIG. 5 to FIG. 7.

(3) First Embodiment of Pattern Observation Method

Figure 5:
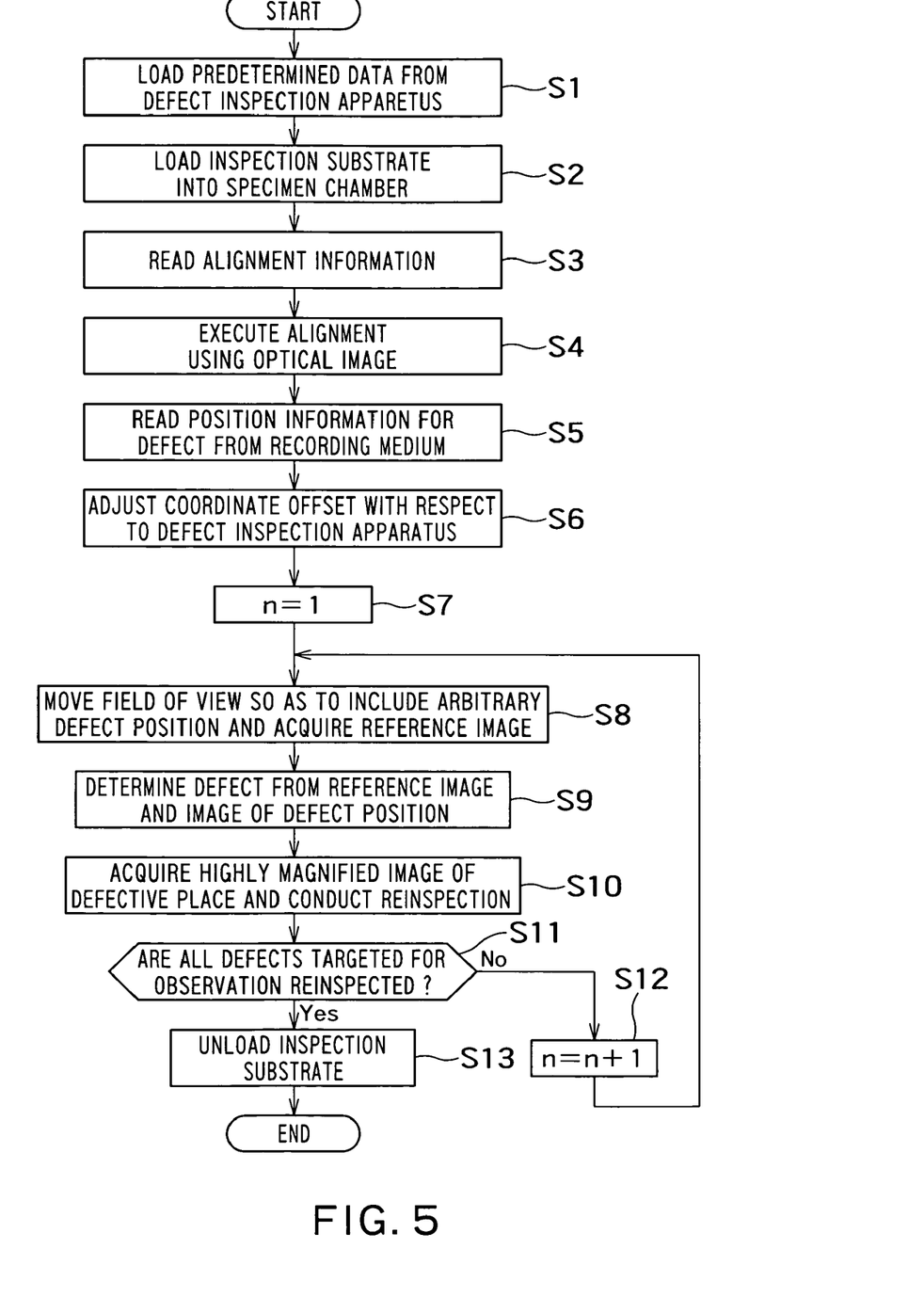
FIG. 5 is a flowchart showing a schematic procedure of a pattern observation method in the first embodiment according to the present invention.
Figure 6A:
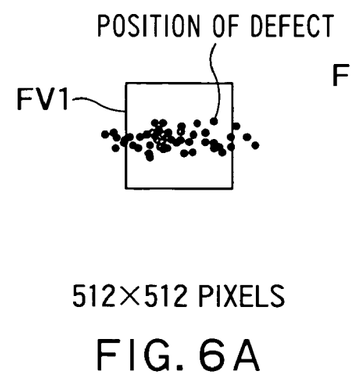
FIGS. 6A to 6C are diagrams showing a pixel configuration according to the pattern observation method in FIG. 5 in comparison with the prior art.

FIG. 5 is a flowchart showing a schematic procedure of a pattern observation method according to the present embodiment. FIGS. 6A to 6C are diagrams showing a pixel configuration according to the present embodiment in comparison with a prior art.

First, as preprocessing, the control computer 50 takes an optical image and coordinate data for a pattern used in the alignment of the inspection substrate S, coordinate data for the detected defect, and data on accuracy distribution of defect position information from the external defect inspection apparatus (not shown) via the communication circuit 70, and then transfers these data to the detachable recording medium MR4 or to the recording medium MR2 (FIG. 5, step S1). The data on the alignment is necessary to share the coordinates of the defect position between the pattern observation apparatus 2 and the external defect inspection apparatus (not shown). The amount of difference of coordinates between these two apparatuses is calculated on the basis of the alignment data, and the coordinate system of the pattern observation apparatus 2 is thus corrected, thereby enabling the reinspection of the defect detected by the external defect inspection apparatus (not shown). It is to be noted that the patterns used for the alignment are preferably cross patterns or patterns whose corner portions are characteristic, and arranged at regular intervals on the inspection substrate S.

Next, the inspection substrate S is loaded into a specimen chamber SC, and vacuum air discharge of the specimen chamber SC is carried out (FIG. 5, step S2). Then, the image data and the coordinate data used for the pattern in the alignment are taken from the data recording medium MR2 to carry out the alignment (step S4). More specifically, the XY stage 22 is driven by the stage control circuit 26 to move to the coordinates of the alignment pattern, and image data of the alignment pattern is acquired and stored in the image memory 34. Next, the image data is transferred to the image processing unit 36 to calculate an amount of difference between the position of the alignment pattern and the center of the image, that is, an amount of difference between the alignment pattern coordinates on the defect inspection apparatus and central coordinates of the SEM image. Then, the XY stage 22 is driven by the stage control circuit 26 to move to the coordinates of the alignment pattern at another position on the inspection substrate S, and similar operation is repeated. The above-mentioned operation is performed for at least two spots, thus carrying out, on the basis of obtained data, the correction of the direct running degree, skew correction and pitch correction of the XY stage 22, rotation correction of the inspection substrate S, and the correction of coordinate offset values ($\Delta x$, $\Delta y$) with respect to the defect inspection apparatus (not shown). This completes the matching of the coordinates of the defect inspection apparatus (not shown) with the coordinates of the pattern observation apparatus 2.

Next, coordinate data for an arbitrary defect detected by the defect inspection apparatus is extracted from the data recording medium MR2 (FIG. 5, step S5), and the XY stage 22 is moved to the position of the defect by the XY stage control circuit 26, and then an SEM image is acquired within a preset field of view and stored in an image memory 15. At this point, because an optical image is used in the above-mentioned alignment, an error corresponding to the resolution of the optical image is caused in the coordinates of the defect. Thus, the target defect is not always located at the center of the SEM image. Therefore, image data of the obtained SEM image is transferred to the image processing unit 36, and a difference between the central position of the defect and the center of the SEM image is calculated, and then the coordinate offset values ($\Delta x$, $\Delta y$) between the defect inspection apparatus (not shown) and the pattern observation apparatus 2 are finely adjusted (FIG. 5, step S6). Adjusted coordinate offset values ($\Delta xc$, $\Delta yc$) between the defect inspection apparatus (not shown) and the pattern observation apparatus 2 are transferred to the control computer 50, and utilized as coordinate correction data during subsequent stage movement. Thus, in the present embodiment, the SEM image with a magnification higher than that of the optical image is used, thereby enabling an accurate adjustment of the coordinate offset. It is therefore possible to significantly improve the accuracy of determining the position of the defect.

Next, a defect which requires a detailed observation with the pattern observation apparatus 2 is selected from the data recording medium MR2, and SEM image data acquired within a preset field of view is transferred to the image processing unit 36 to extract the defect. The extraction of the defect is carried out by comparing an SEM image centering on coordinates where the defect is present with an SEM image (reference image) of another place where no defect is present. The reference image is generally set in an adjacent die. First, n=1 is set (FIG. 5, step S7) so that the field of view is moved so as to include an arbitrary defect position, and an SEM image is acquired at that position, and then an SEM image is acquired with respect to a die adjacent to the defect position and used as the reference image (FIG. 5, step S8). Then, the SEM image at the defect position is compared with the reference image to determine whether or not there is a defect (FIG. 5, step S9). If a defect is specified, the magnification is increased, that is, the field of view is narrowed with a central focus on the position of the specified defect so as to again acquire an SEM image of the defective portion, and the defect is observed in more detail (FIG. 5, step S10). The above-mentioned operation is repeated as many times as the number of defects to be observed (FIG. 5, steps S11, S12, S8 to S10), and the inspection substrate S is unloaded when the reinspection is finished (FIG. 5, step S13).

The field of view when the defect is extracted is decided considering the coordinate accuracy of the pattern observation apparatus 2, the above-mentioned alignment accuracy, and the defect position accuracy of the external defect inspection apparatus (not shown). For example, the amount of defect position difference on the SEM image is $(1.5^2+2^2+4^2)^{1/2}=4.7$ µm if the coordinate accuracy of the pattern observation apparatus 2 is +/−1.5 µm, the alignment accuracy is +/−2 µm, and the defect position accuracy is +/−4 µm. Therefore, as shown in FIG. 6A, the field of view FV1 in this case is +/−5 µm=10 µm square, and the number of pixels is 512×512. Here, the defect position accuracy of the defect inspection apparatus has a habit, and if the position accuracy is +/−8 µm in an X direction and +/−4 µm in a Y direction, the amount of defect position difference in the Y direction on the SEM image is 4.7 µm as described above, while the amount of defect position difference in the X direction is $(1.5^2+2^2+8^2)^{1/2}=8.4$ µm. Thus, as shown in FIG. 6C, a field of view FV12 in this case is set at 20 µm×10 µm, and the number of pixels is 1024×512.

Figure 6B:
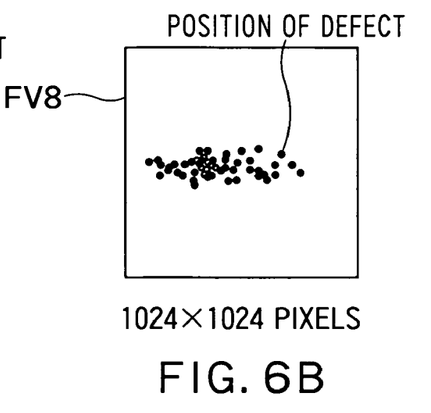
Figure 6C:
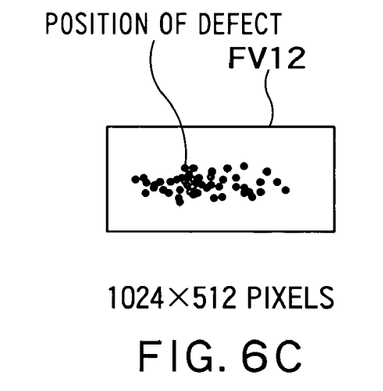
Figure 7:
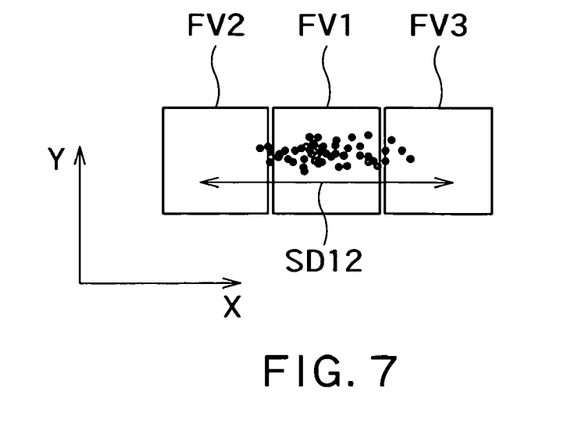
FIG. 7 is an explanatory diagram of the searching method when a defect can not be detected in a second embodiment of the pattern observation method according to the present invention.

In the method according to the prior art, the number of pixels needs to be 1024×1024 as shown in the field of view FV8 of FIG. 6B in order to have a field of view of 20 µm×20 µm without changing the resolution of the image, that is, the size per image. Moreover, if the field of view is enlarged to 20 µm×20 µm so that the number of pixels remains at 512×512, the throughput does not decrease but the size per image is doubled, and there has thus been an adverse effect that causes increase of minimum detected defect size.

On the contrary, the present embodiment only requires a field of view of 20 µm×10 µm and the number of pixels of 1024×512, and it is therefore possible to reduce the time of scanning in the field of view with the electron beam, that is, the image acquiring time to half of that in the conventional technique without changing the size per pixel.

Thus, according to the present embodiment, since the position accuracy data of the external defect inspection apparatus is used to optimize the set value of the field of view or the number of pixels in the reinspection of the defect, it is possible to simultaneously accomplish the reduction of re-detection time and the improvement of a re-detection ratio.

It is to be noted that the SEM image obtained by the application of the electron beam to the region in the vicinity of the defective place is used as the reference image in the present embodiment, but the present invention is not limited thereto. For example, a reference image is created from the design data in advance and stored in the data recording medium MR2, and this reference image may be properly taken and compared with an inspection image to perform a reinspection of an abnormality.

(4) Second Embodiment of Pattern Observation Method

The view field size is enlarged in an x direction in the first embodiment described above. However, if it is previously known that a defect position accuracy in the x direction is poor, then the view field size is kept unchanged at 512×512, and a field of view is moved in the x direction over a distance corresponding to one image to acquire an image only when no defect can be detected in the current field of view, such that the defect can be simply and rapidly detected. FIG. 7 is an explanatory diagram of a searching method according to a pattern observation method of the present invention. In an example shown in FIG. 7, when any defect can not be detected in a first observation view field FV1, a move is made from a field FV2 to a view field FV3 (→FV2) in accordance with a search direction SD12 in the X direction, thereby acquiring an image. The search direction is previously specified or priority is previously set to the search directions, such that it is possible to significantly reduce the detection time of the defect as compared with that in the method of the prior art in which all the adjacent regions in eight directions shown in FIG. 3 are searched. The pattern observation method of the present embodiment is especially effective when, for example, the aspect ratio of an image is high and scanning is difficult due to a limitation of a deflection circuit for an electron beam, or when a trouble is caused in defect detection processing due to a limitation of an image processing apparatus.

Thus, according to the present embodiment, since position accuracy data of an external defect inspection apparatus is used to optimize the search direction when no defect can be detected, it is possible to simultaneously accomplish the reduction of re-detection time and the improvement of a re-detection ratio.

(5) Program

A series of procedures of the pattern observation method described above may be stored, for example, in the form of a recipe file in a recording medium such as a flexible disk or a CD-ROM as a program to be executed by a computer, and may be read into and executed by the computer. This makes it possible to achieve the pattern observation method according to the present invention by use of a general-purpose control computer.

Figure 8:
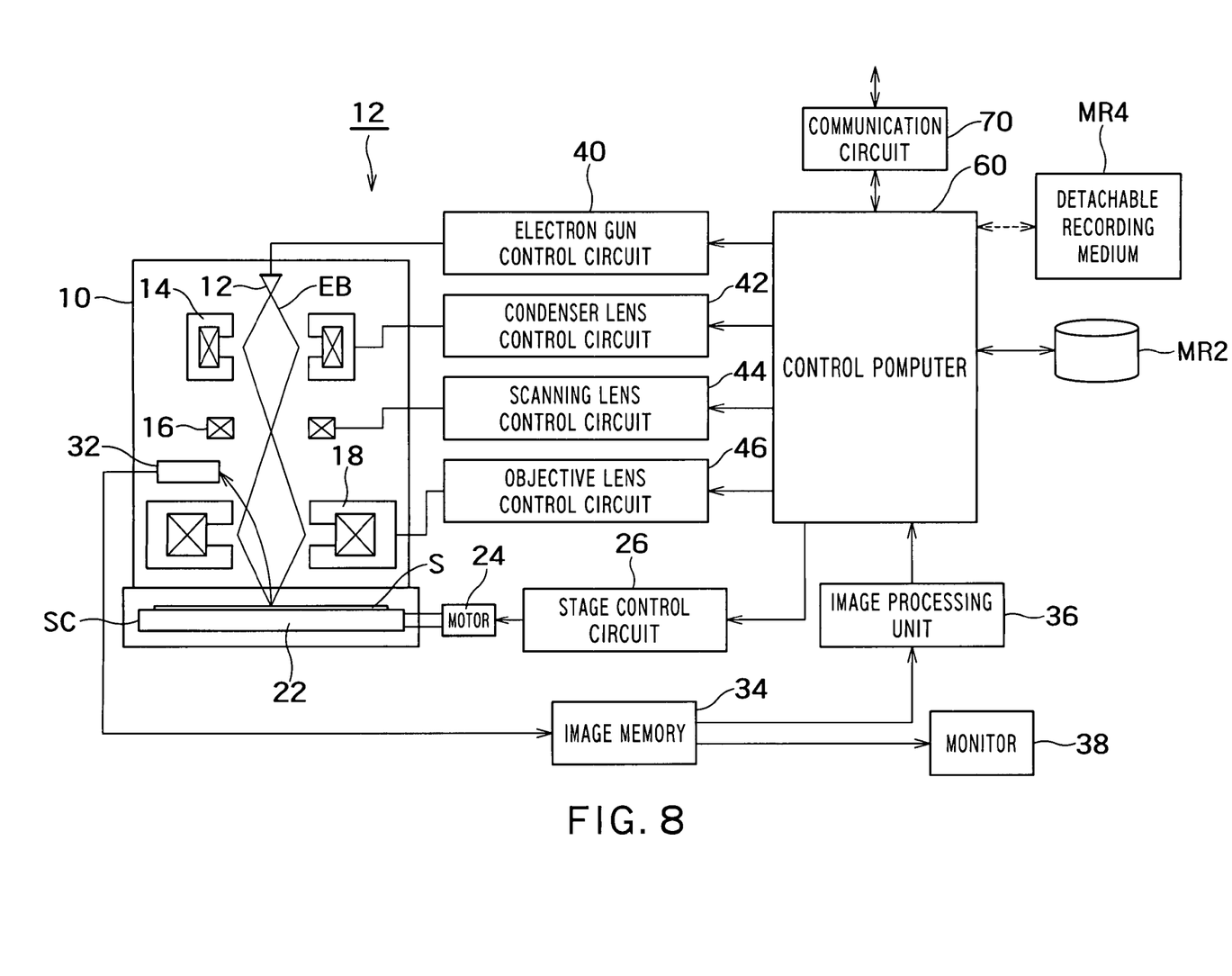
FIG. 8 is a block diagram showing a schematic configuration of the pattern observation apparatus which executes pattern observation in conformity to one embodiment of a program according to the present invention.

FIG. 8 is a block diagram showing a schematic configuration of a pattern observation apparatus which executes pattern observation in conformity to one embodiment of a program according to the present invention. A pattern observation apparatus 12 shown in FIG. 8 is an application of a scanning electron microscope similar to the pattern observation apparatus 2 in FIG. 4, and is different from the pattern observation apparatus 2 in FIG. 4 in that it comprises a general-purpose control computer 60 instead of the control computer 50 including the view field size adjusting circuit and the search direction deciding circuit. Moreover, in the present embodiment, an image processing unit 36 comprises an image processing computer. In other respects, the configuration of the pattern observation apparatus 12 is substantially the same as that of the pattern observation apparatus 2 in FIG. 4. In the present embodiment, the control computer 60 and the image processing unit 36 correspond to, for example, computers connected to a charged particle microscope. In the pattern observation apparatus 12, the series of procedures of the pattern observation method described above is once stored in the form of a recipe file in, for example, the detachable recording medium MR4 and in the recording medium MR2 via the communication circuit 70, and read by the control computer 60 at every detection of a defect, thereby executing the pattern observation described in the above embodiment.

Here, the recording medium MR2 is not limited to a fixed recording medium such as a hard disk drive or a memory, and may be a portable medium such as a magnetic disk or an optical disk. Further, the program incorporating the series of procedures of the pattern observation method described above may be distributed to a plurality of pattern observation apparatuses via a communication line (including wireless communication) such as the Internet. Moreover, the program incorporating the series of procedures of the pattern observation method described above may be distributed in an encrypted, modulated or compressed state via a wired line such as the Internet or a wireless line or in a manner stored in a recording medium.

(6) Method of Manufacturing Semiconductor Device

If at least one of the pattern observation methods according to the present invention described above is executed in a process of manufacturing a semiconductor device, pattern observation with a high throughput is enabled, thereby making it possible to manufacture the semiconductor device with a high yield ratio.

What is claimed is:

1. A pattern observation apparatus comprising:
a defect position information input unit which downloads defect position information for a pattern formed in a specimen and defect position accuracy information of an external inspection apparatus, the defect position information having been detected by the external inspection apparatus, the defect position accuracy having direction dependency that is derived from a difference between an actual position of a defect and a position of the defect detected by the external inspection apparatus, the difference resulting from poor accuracy of the external inspection apparatus in a particular direction;
a moving unit which moves the specimen so as to bring a place detected as defective by the inspection apparatus into a field of view on the basis of the defect position information;
a charged particle source which generates a charged particle beam and applies the charged particle beam to the specimen;
a signal processing unit which detects at least one of secondary charged particles, reflected charged particles and back scattering charged particles emitted from the specimen due to the application of the charged particle beam and which outputs data on an inspection image of a specimen surface in the defective place;
an inspection unit which re-detects an abnormality of the place detected as defective, on the basis of the inspection image; and
a view field adjusting unit which adjusts a size of the field of view or a moving direction of the specimen on the basis of the direction dependency of the defect position accuracy of the external inspection apparatus while a resolution of the inspection image is kept fixed.

2. The pattern observation apparatus according to claim 1, wherein the view field adjusting unit changes the size of the field of view in a first direction independently from a second direction, the first and second directions being perpendicular to each other to constitute two dimensions.

3. The pattern observation apparatus according to claim 1, wherein the view field adjusting unit changes the size of the field of view so that the field of view is enlarged in a direction in which the accuracy of the external inspection apparatus is poorer than other direction.

4. The pattern observation apparatus according to claim 1, wherein the view field adjusting unit controls the moving unit so that the specimen is moved in a direction on which the position accuracy of the external inspection apparatus depends when no abnormality is detected in the place detected as defective.

5. The pattern observation apparatus according to claim 4, wherein the view field adjusting unit preferentially selects a direction in which the accuracy of the external inspection apparatus is poorer than other direction as the direction on which the position accuracy of the external inspection apparatus depends.

6. A pattern observation method comprising:
acquiring defect position information having been obtained by a first inspection apparatus for a pattern formed in a specimen from the first inspection apparatus and defect position accuracy information of the first inspection apparatus, the defect position accuracy having direction dependency that is derived from a difference between an actual position of a defect and a position of the defect detected by the external inspection apparatus, the difference resulting from poor accuracy of the first inspection apparatus in a particular direction:
moving a specimen within a second inspection apparatus on the basis of defect position information and generating a charged particle beam at a position where a place detected as defective by the first inspection apparatus comes into a field of view of the second inspection apparatus to apply the charged particle beam to the specimen;
detecting at least one of secondary charged particles, reflected charged particles and back scattering charged particles emitted from the specimen due to the application of the charged particle beam to acquire an inspection image of a specimen surface in the place detected as defective;
re-detecting an abnormality of the place detected as defective on the basis of the inspection image; and
adjusting a size of the field of view of the second inspection apparatus or a moving direction of the specimen in the second inspection apparatus on the basis of direction dependency of defect position accuracy of the first inspection apparatus while a resolution of the inspection image is kept fixed.

7. The pattern observation method according to claim 6, wherein the size of the field of view in a first direction is changed independently from a second direction the first and second directions being perpendicular to each other to constitute two dimensions.

8. The pattern observation method according to claim 6, wherein the size of the field of view is changed so that the field of view is enlarged in a direction in which accuracy is poorer than other direction.

9. The pattern observation method according to claim 6, wherein the specimen is moved in a direction on which the position accuracy of the first inspection apparatus depends when no abnormality is detected in the place detected as defective.

10. The pattern observation method according to claim 9, wherein the direction in which the accuracy of the first inspection apparatus is poorer than other direction is preferentially selected as the direction on which the position accuracy of the first inspection apparatus depends.

11. A program which is stored in a computer-readable medium connectable to a charged particle microscope and which causes the computer to execute a pattern observation method, said pattern observation method comprising:
acquiring defect position information having been obtained by a first inspection apparatus for a pattern formed in a specimen from the first inspection apparatus and defect position accuracy information of the first inspection apparatus, the defect position accuracy having direction dependency that is derived from a difference between an actual position of a defect and a position of the defect detected by the external inspection apparatus, the difference resulting from poor accuracy of the first inspection apparatus in a particular direction;
moving a specimen within a second inspection apparatus on the basis of defect position information and generating a charged particle beam at a position where a place detected as defective by the first inspection apparatus comes into a field of view of the second inspection apparatus to apply the charged particle beam to the specimen;
detecting at least one of secondary charged particles, reflected charged particles and back scattering charged particles emitted from the specimen due to the application of the charged particle beam to acquire an inspection image of a specimen surface in the place detected as defective;
re-detecting an abnormality of the place detected as defective on the basis of the inspection image; and
adjusting a size of the field of view of the second inspection apparatus or a moving direction of the specimen in the second inspection apparatus on the basis of direction dependency of defect position accuracy of the first inspection apparatus while a resolution of the inspection image is kept fixed.

12. The program according to claim 11, wherein the size of the field of view in a first direction is changed independently from a second direction, the first and second directions being perpendicular to each other to constitute two dimensions.

13. The program according to claim 11, wherein the size of the field of view is changed so that the field of view is enlarged in a direction in which accuracy is poorer than other direction.

14. The program according to claim 11, wherein the specimen is moved in a direction on which the position accuracy of the first inspection apparatus depends when no abnormality is detected in the place detected as defective.

15. The program according to claim 14, wherein the direction in which the accuracy of the first inspection apparatus is poorer than other direction is preferentially selected as the direction on which the position accuracy of the first inspection apparatus depends.

16. A method of manufacturing a semiconductor device comprising a pattern observation method, said pattern observation method including:
acquiring defect position information having been obtained by a first inspection apparatus for a pattern formed in a specimen from the first inspection apparatus and defect position accuracy information of the first inspection apparatus, the defect position accuracy having direction dependency that is derived from a difference between an actual position of a defect and a position of the defect detected by the external inspection apparatus, the difference resulting from poor accuracy of the first inspection apparatus in a particular direction;
moving a specimen within a second inspection apparatus on the basis of defect position information and generating a charged particle beam at a position where a place detected as defective by the first inspection apparatus comes into a field of view of the second inspection apparatus to apply the charged particle beam to the specimen;
detecting at least one of secondary charged particles, reflected charged particles and back scattering charged particles emitted from the specimen due to the application of the charged particle beam to acquire an inspection image of a specimen surface in the place detected as defective;

re-detecting an abnormality of the place detected as defective on the basis of the inspection image; and adjusting a size of the field of view of the second inspection apparatus or a moving direction of the specimen in the second inspection apparatus on the basis of direction dependency of defect position accuracy of the first inspection apparatus while a resolution of the inspection image is kept fixed.

17. The method of manufacturing a semiconductor device according to claim 16, wherein the size of the field of view in a first direction is changed independently from a and second direction, the first and second directions being perpendicular to each other to constitute two dimensions.

18. The method of manufacturing a semiconductor device according to claim 16, wherein the size of the field of view is changed so that the field of view is enlarged in a direction in which accuracy is poorer than other direction.

19. The method of manufacturing a semiconductor device according to claim 16, wherein the specimen is moved in a direction on which the position accuracy of the first inspection apparatus depends when no abnormality is detected in the place detected as defective.

20. The method of manufacturing a semiconductor device according to claim 19, wherein the direction in which the accuracy of the first inspection apparatus is poorer than other direction is preferentially selected as the direction on which the position accuracy of the first inspection apparatus depends.

* * * * *